Figure 1:
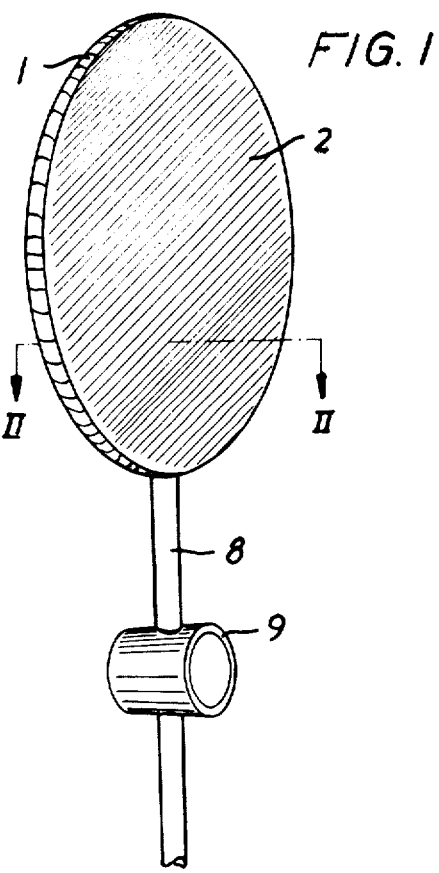

United States Patent [19]

Madsen

[11] 4,125,012

[45] Nov. 14, 1978

[54] APPARATUS FOR MEASURING THERMAL DISCOMFORT ORIGINATING FROM ASYMMETRY IN THE THERMAL FIELD OR VARIATIONS WITH TIME OF THE THERMAL INFLUENCE ON THE SKIN

[76] Inventor: Thomas L. Madsen, No. 11 Rosengårdsvej, 2830 Virum, Denmark

[21] Appl. No.: 697,757

[22] Filed: Jun. 21, 1976

[30] Foreign Application Priority Data

Jun. 25, 1975 [DE] Fed. Rep. of Germany ....... 2528340
Nov. 17, 1975 [DK] Denmark ............................. 5159/75

[51] Int. Cl.² ............................................. G01N 25/00
[52] U.S. Cl. .................................... 73/15 R; 73/190 H
[58] Field of Search ................... 73/15 R, 204, 339 C, 73/355, 432 SD, 190 R, 190 H

[56] References Cited

U.S. PATENT DOCUMENTS

| | | | |
|---|---|---|---|
| 3,256,734 | 6/1966 | Storke, Jr. ............................... | 73/190 |
| 3,367,182 | 2/1968 | Baxter ..................................... | 73/190 |
| 3,605,494 | 9/1975 | Progelhof et al. ...................... | 73/190 |
| 3,664,193 | 5/1972 | Nielsen ................................... | 73/355 |
| 3,688,558 | 9/1972 | Tixier ...................................... | 73/15 |
| 3,878,728 | 4/1975 | Marzetta ................................. | 73/15 |
| 3,928,800 | 12/1975 | Strenglein ............................... | 73/190 |

OTHER PUBLICATIONS

Toy et al., "A Surface Plate Colorimeter" in J. Phys. E. (G. Br.), vol. 6, #8 (8/73), pp. 702–704.

Primary Examiner—Herbert Goldstein
Attorney, Agent, or Firm—Stevens, Davis, Miller & Mosher

[57] ABSTRACT

An apparatus for measuring thermal discomfort originating from an asymmetry in a thermal field comprises two blackened surfaces facing in opposite directions and maintained at a common temperature higher than that of the surrounding air. The difference in power required to maintain the same higher temperature of the two surfaces is measured and is an expression of the thermal discomfort. If the thermal influence varies with time the probe may have the same thermodynamic characteristics as the human skin or these characteristics can also be obtained by an electric filter.

4 Claims, 7 Drawing Figures

APPARATUS FOR MEASURING THERMAL DISCOMFORT ORIGINATING FROM ASYMMETRY IN THE THERMAL FIELD OR VARIATIONS WITH TIME OF THE THERMAL INFLUENCE ON THE SKIN

The invention relates primarily to an apparatus for measuring thermal discomfort originating from an asymmetry of a thermal field, the apparatus comprising a probe having heating and temperature measuring means as well as a control and measuring equipment connected to the probe for determining the heat exchange between the probe and the surroundings. The published German patent application No. DT-OS No. 2,157,550 indicates an apparatus for measuring a person's thermal discomfort, that is to say the deviations from the ideal state of comfort, where the heat, which by the combustion of the food is dosed in the body, is given off to the surroundings while a comfortable skin temperature is maintained. In the case of this prior art apparatus, however, no regard is paid to a possible asymmetry of the thermal field originating, for example, from surfaces which are essentially colder or warmer than the mean temperature or from a high air velocity, that is to say a draft.

It would therefore be desirable to provide an apparatus for ascertaining the thermal discomfort originating from asymmetry in the thermal field.

A probe is known for the directional measurement of the heat exchange between a surface on the probe and the surroundings. If the said surface has such a color that its heat radiation corresponds to that of the skin and if it is kept at skin temperature it is possible by means of the known probe to obtain certain information regarding the heat exchange between the surface of a human body and the surroundings in a given direction. If it is desired to use the known probe for ascertaining the asymmetry of the thermal field a series of measurements must be performed with the probe pointing in different directions. Since the measurement in each direction can only be performed after the expiration of some time, since an equilibrium must first be found, the use of the known probe becomes complicated and measurements takes a long time, additionally the measurements cannot be very accurate since the thermal field has time to change during the performance of the measurements.

The object of the present invention is to provide an apparatus with which it is possible to perform measurements of thermal discomfort originating from an asymmetry in the thermal field rapidly and simply. According to the invention, this task is accomplished by a probe comprising two plate-shaped elements which are mounted parallel to each other and are heat-insulated from each other. The surfaces of these elements face away from each other and are blackened. The control and measuring equipment is arranged to keep the black surfaces at approximately the same temperature while measuring the difference between the power required for each surface for this purpose. In this case, a direct measurement is performed of the difference between the heat exchange between the probe and the surroundings in two opposite directions so that it is possible rapidly and by means of only one measurement to obtain information relating to the asymmetry of the thermal field. Since the measurements in the opposite directions are performed simultaneously, one may be sure that errors originating from conditions varying with time have been precluded.

For reasons of dispersion it may according to the invention be expedient that each plate-shaped element be divided into several separate parts. This is of particular importance if the apparatus is arranged for also measuring other phenomena than the discomfort originating from the asymmetry, cf. the following.

With a view to obtaining a reference basis for the temperatures of the black surfaces an embodiment of the apparatus according to the invention is characterized in that it comprises means for measuring the air temperature and in that the control and measuring equipment is arranged for keeping a fixed temperature difference between the temperatures of the air and the black surfaces. The difference in temperatures may for example be 15° C., whereby the black surfaces at an air temperature of about 20° C. obtain a temperature corresponding approximately to the skin temperature of the human body.

For measuring the temperatures of the air and the black surfaces the apparatus according to the invention may comprise temperature-sensitive resistors inserted into bridge circuits, from which voltages for controlling the powers supplied to the plate-shaped elements are derived. Thus, a regulation of the temperatures of the black surfaces is achieved in a particularly simple way.

A particularly expedient embodiment of the apparatus according to the invention is characterized in that heating of the plate-shaped elements is effected by pulse trains having constant frequencies and amplitudes, but variable pulse widths, and in that the control and measuring equipment comprises a moving coil instrument having a central zero point, to which the two pulse trains are supplied. In this case a tremendous advantage is gained in that the deflection on the moving coil instrument will be a direct expression of the difference of the heating effects supplied to the two black surfaces.

The limits of the discomfort, which a person will sense by asymmetry in the thermal field, will depend on the activity level of the person, and consequently a variable resistor for setting the activity level may be connected in parrallel with the moving coil instrument.

The clothing of the person will also be decisive of the degree of asymmetry that can be tolerated without discomfort, and to pay due regard to this factor the scale of the instrument may, according to the invention, be so designed that the degree of asymmetry can be read for different clothing values (clo-values).

The invention also relates to the direct measurement of thermal discomfort originating from a draft e.g. from air-conditioning systems.

It is well-known that air velocity can be measured by determining its cooling effect on a heated wire or surface. However, this is not sufficient when the degree of thermal discomfort caused by a draft is to be measured.

New investigations have shown that although people remain in thermal comfort in thermal fields of even considerable asymmetry, when only the heat balance is in order, this does not apply if the thermal influence is not stationary. Investigations indicate that the tolerance for local variations in heat dissipation is at a minimum when these variations occur at frequencies in the area 0.1–1.0 Hz. It has been known for a long time that the physical parameter determining the local sensation of heat and cold is the variation itself of the temperature gradient (or the heat current) through the skin. It is this variation which is registered by the thermoreceptors of the skin.

Based on existing knowledge on the thermal-physical characteristics of the skin and on the geometrical position of the thermoreceptors, the frequency of a given external thermo-influence which will give a maximum influence on the thermoreceptors can be calculated. It has turned out that this frequency lies in the region 0.1–1.0 Hz.

Therefore, it can reasonably be assumed that the high sensitivity to draft is due to the fact that it leads to a maximum influence on the thermoreceptors of the skin.

It is an object of the invention to provide an apparatus by which it is possible to measure thermal discomfort originating from varying thermal influences (draft). This object is attained by means of a probe, which has the same thermodynamic characteristics as the human skin, that is, it corresponds to the thermal characteristics of skin. The sensing element of the probe which controls the amount of heat yielded is positioned in the place normally occupied by the thermoreceptors in the thermal system. As a result, the variation in the power supplied to the probe for heating the same will vary with the same frequency and amplitude as thermal signals normally sensed by the thermoreceptors in the skin. It is then possible by a simple electric network to transform the electrical signal of the probe to the deflection of a pointer, which will be proportional to the signal normally sent from the thermoreceptors to the brain relating to the sensation of cold and heat.

Figure 2:
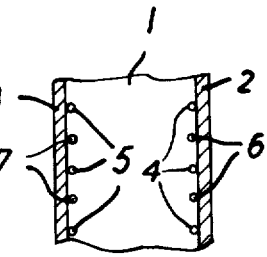
Figure 5:
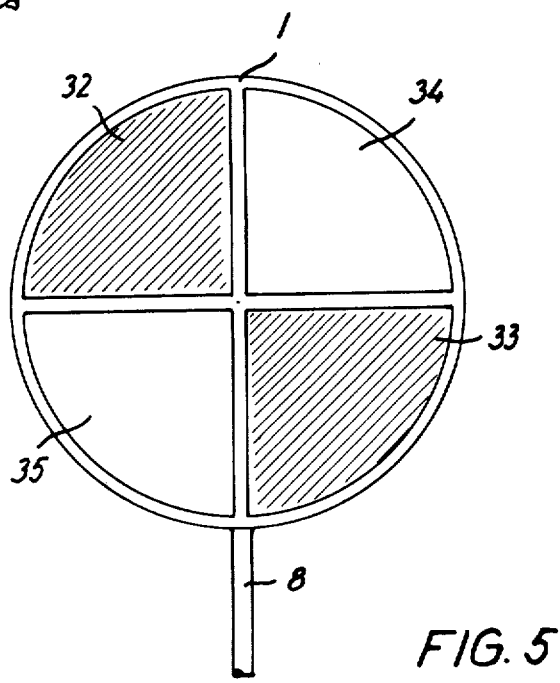
Figure 3:
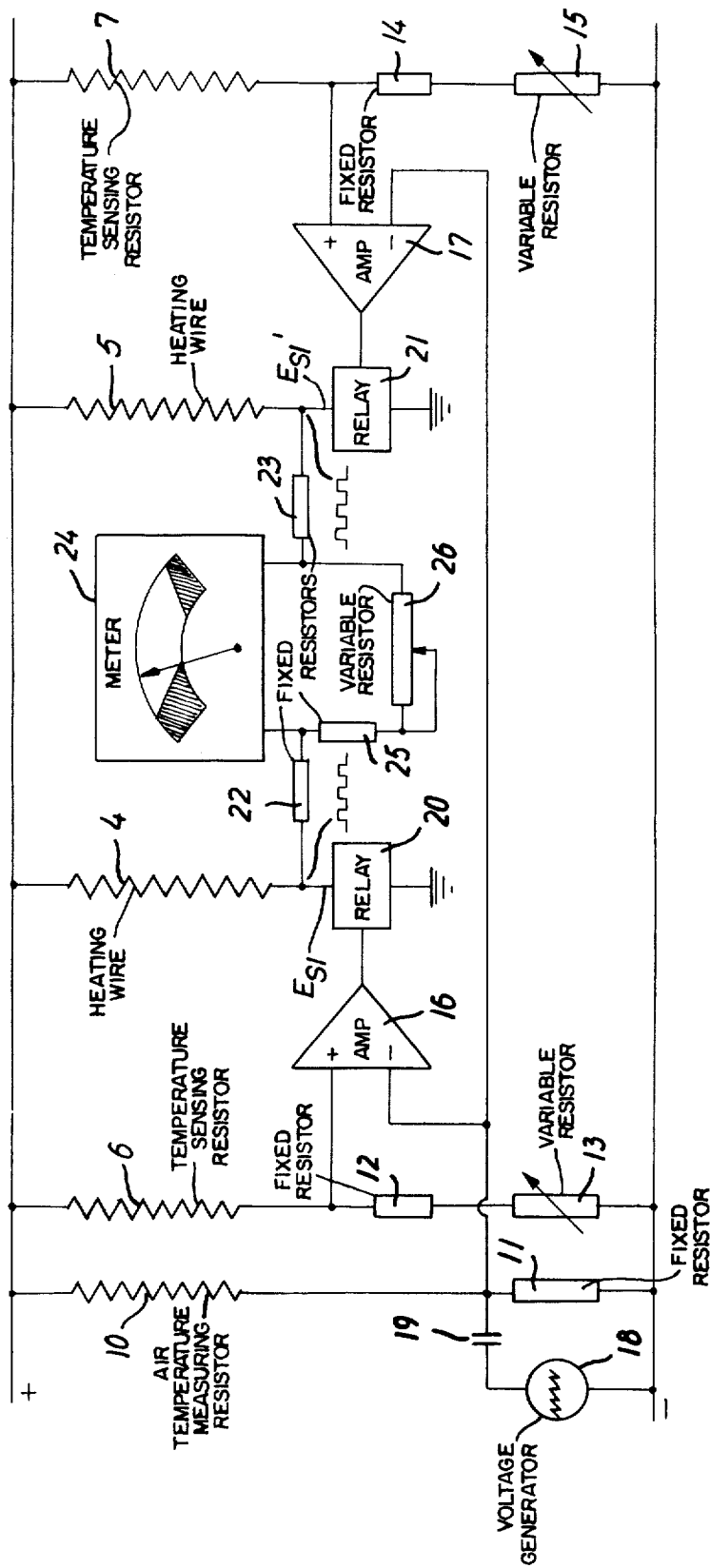
Figure 4:
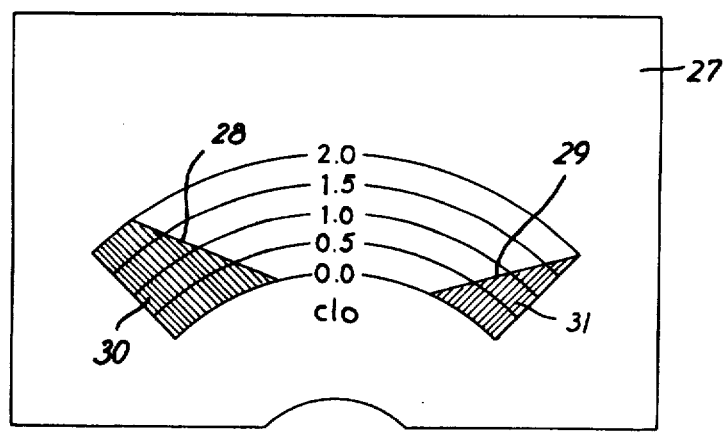
Figure 6:
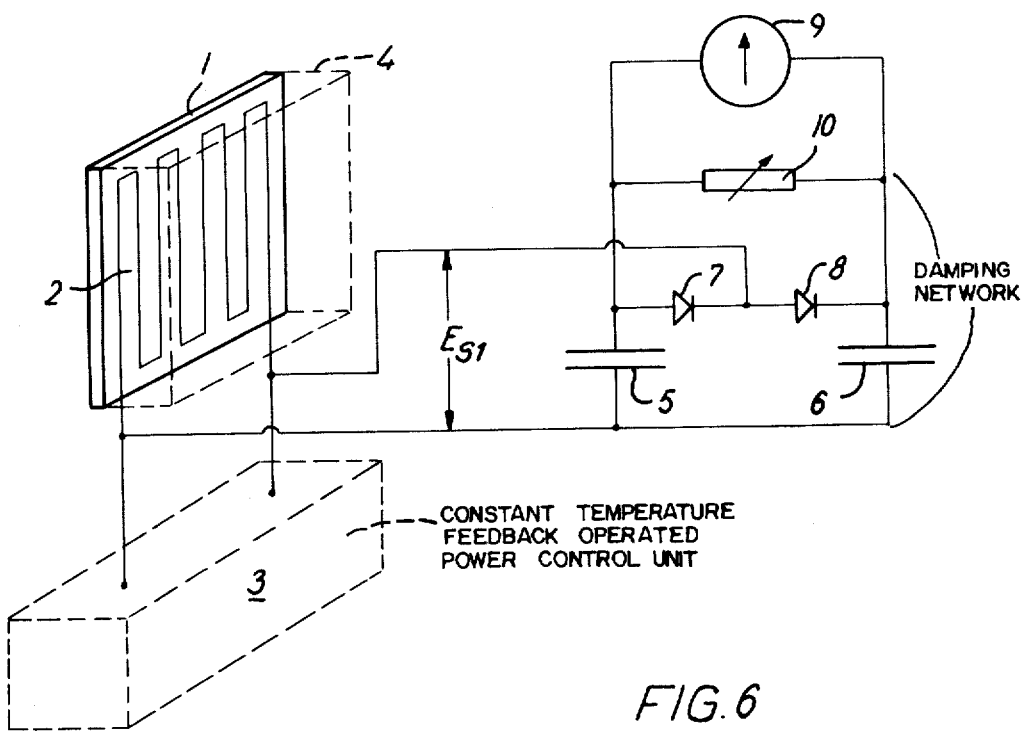
Figure 7:
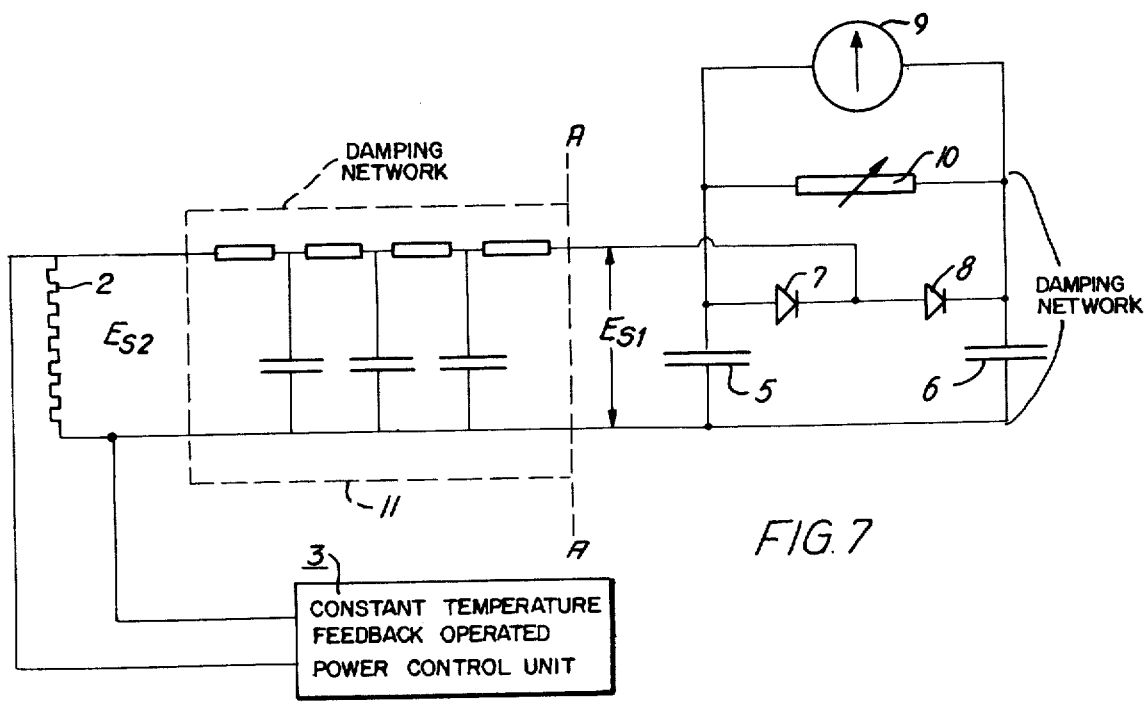

Below, the invention is explained in greater detail with reference to the schematical drawing in which:

FIG. 1 in perspective view shows a probe for an apparatus according to the invention, FIG. 2 on a much enlarged scale shows a section through part of the probe shown in FIG. 1, FIG. 3 shows a circuit diagram of an apparatus according to the invention, FIG. 4 shows a scale for a measuring instrument in the apparatus shown in FIG. 3, FIG. 5 shows another embodiment of a probe for an apparatus according to the invention, FIG. 6 shows another embodiment of an apparatus according to the invention and FIG. 7 shows a slightly changed embodiment.

The maintenance of thermal comfort requires, firstly, that the heat balance between a person and the surroundings is as it should be. The published German patent application No. DT-OS No. 2.157.550 mentions an apparatus with which it can be ascertained whether a person's thermal comfort is optimum, corresponding to a PMV-value of zero, or whether it deviates therefrom to a greater or smaller degree. A deviation from the optimum may for example be due to the fact that the heat emission from the different parts of the body differs, this causing a thermal discomfort.

With the apparatus according to the invention it is possible rapidly and simply to ascertain whether an asymmetry of the thermal field exists and whether this asymmetry is so great that it can cause thermal discomfort. The thermal discomfort originating from an asymmetrical field may be due to an asymmetrical heat emission either by radiation or by convection or by a combination of the two. However, a person is not normally able to ascertain whether asymmetrical radiation or asymmetrical convection (draft) is concerned since the thermoreceptors of the skin are located below the surface and register differences in the flow of heat through the skin, that is to say heat conduction.

The invention is based on the following expression of the comfort limits to asymmetrical thermal fields:

$$-2.4 - 1.8 I_{clo} \leq t_W F_{P-W} \leq 3.9 + 1.8 I_{clo}, \qquad (I)$$

where $I_{clo}$ is the clo-value of the clothing, $F_{P-W}$ is the projected area factor between person and radiation source and $t_w$ is the difference in temperatures between radiation source and mean radiation temperature.

The expression applies when the PMV-value is zero. If this is not the case, the region is narrowed. When forming the expression, asymmetrical radiation fields have been used, which is of no importance, however, since, as mentioned above, a person cannot feel what is the cause of the asymmetry. The expression is determined empirically on the basis of a comparatively small number of people, and the figures may therefore be changed when more extensive empirical material is available.

The probe shown in FIGS. 1 and 2 for an apparatus according to the invention comprises a plate 1 of heat-insulating material which on either side is provided with a plate 2 and 3 of good heat-conducting material, e.g. silver. The surfaces of the plates 2 and 3 facing the surroundings have been made black and dull or otherwise prepared to have substantially the same thermal characteristics, e.g. radiation emission number, as human skin. On their backs the plates 2 and 3 are provided with heating wires 4 and 5 as well as temperature-sensitive resistance wires 6 and 7, e.g. nickel wires. The wires may be secured to the plates by adhesion.

The unit composed of the plates 1, 2 and 3 is mounted on a rod 8 which in addition carries an air temperature measuring device 9 which contains a temperature-sensitive resistance wire, not shown in FIG. 1, for example a nickel wire, and which may furthermore comprise a small fan which provides an effective air circulation around the resistance wire and thereby a rapid and precise measurement of the air temperature. The air temperature measuring device 9 must be placed as closely as possible to the radiation measuring device 1, 2, 3, but in such a way that the measurements do not interfere with each other. Of course, device 9 need not be mounted on rod 8.

The heating wires 4 and 5, the resistance wires 6 and 7 as well as the resistance wire 10 in the air temperature measuring device 9 are via leads, not shown, inserted into the equipment shown in FIG. 3. In series with a fixed resistor 11 the air temperature measuring resistor 10 constitutes one branch of two bridge circuits, the other branches of which are constituted by the resistor 6 in series with a fixed resistor 12 and a variable resistor 13 and the resistor 7 in series with a fixed resistor 14 and a variable resistor 15, respectively. In the bridge diagonals, amplifiers 16 and 17 are inserted which operate as comparison circuit arrangements having one input additionally supplied with a triangular voltage from a voltage generator 18 via a capacitor 19. The output signals from the amplifiers 16 and 17 control two, preferably electronic, relays 20 and 21 with which the heating bodies 4 and 5 can be connected to the DC supply voltage of the circuit arrangement. With this arrangement the heating elements are supplied with a pulse voltage (square wave) having a fixed frequency, viz. determined by the frequency of the triangular voltage, and having a fixed amplitude, viz. determined by the DC supply voltage of the circuit arrangement, and having a variable pulse width which is dependent on the voltage of the particular bridge diagonal. If the voltage across the heating elements 4 or 5 is measured with a moving coil instrument, a deflection is obtained which is proportional to the power supplied to the heating elements. In this regard reference is made to U.S. Pat. No. 3,751,634.

In the circuit arrangement shown in FIG. 3 the voltages $E_{S1}$ and $E_{S1}'$ across the two heating elements are via resistors 22 and 23 supplied to a moving coil instrument 24 having its zero point at the middle of the scale. The reading of this instrument will consequently be proportional to the difference between the power supplied ot the two heating elements.

The instrument 24 is shunted by the series-connection of a fixed resistor 25 and a variable resistor 26 with which the sensitivity of the instrument can be varied. The resistor 26 is set in conformity with the discomfort value, that is to say PMV-value, measured for example with the apparatus known from the published German patent application mentioned above, which value could be termed the direction-independent discomfort value, since a person present in an asymmetrical thermal field more easily reaches the limits given by the expression (I) if an essential direction-independent discomfort is concerned than if the direction-independent state of comfort is optimum.

When the apparatus is to be used, the two resistors 13 and 15 are, preferably in a stationary thermal field, set at such values that the two plates 2 and 3 are at a temperature which is a fixed number of degrees, e.g. 15° C., above the air temperature which is measured with the resistor 10. When the probe is subsequently subjected to varying thermal field, e.g. draft, the circuit arrangement shown in FIG. 3 will tend to maintain the same temperature relations between the air temperature and the temperature of the two plates 2 and 3, and the difference in heating power required for this purpose can be read on the instrument 24.

The object is now to determine the points on the scale of the instrument corresponding to the limits in the expression (I). When a person senses a thermal discomfort, that is, when these limits are exceeded, the reason for this is that a too large local deviation from the mean skin temperature is sensed as a discomfort. By letting one side of the probe represent the normal skin temperature while the other side measures the deviation therefrom it may be ascertained whether the expression (I) has been fulfilled.

The expression $\Delta t_W F_{P-W}$ can be calculated if the temperature of the radiation source causing the asymmetry and the person's projected area factor to this radiation source are known. In the case of the probe the radiation conditions are simpler. It simply divides the surroundings into two half spaces. If the said radiation source is supposed to be located in half space I, the expression $$\Delta t_W F_{P-W} = (t_{mrt_I} - t_{mrt_{II}}) \, 0.5 \tag{II}$$

is obtained, where the left side of the sign of equation applies to a person and the right side to the probe, and where $t_{mrt_I}$ and $t_{mrt_{II}}$ designate the mean radiation temperatures for one and the other half space, respectively. The factor 0.5 is due to the fact that each of the probe plates has a total projected area factor to the surroundings of 0.5.

If $I_{clo}$ is assumed to be equal to zero, the following expression $$-4.8 \leq t_{mrt_I} - t_{mrt_{II}} \leq 7.8 \tag{III}$$

is obtained by the insertion of the expression (II) into the expression (I).

Since the heat exchange between a surface and the surroundings is represented by $$\phi = \epsilon \times \tau(t_F^4 - t_{mrt}^4) \tag{IV}$$

where
- $\epsilon$ is the emission figure for the surface (which in the case of a black dull surface is equal to 0.97),
- $\tau$ is Stefan Boltzmann's constant (5.75 × 10$^{-8}$ W/m$^2$ × Kelvin),
- $t_F$ is the temperature of the surface (in Kelvin) and
- $t_{mrt}$ is the mean radiation temperature of the surroundings (likewise in Kelvin) it is now possible to find the differences in heat exchange from the two sides of the probe which correspond to the upper and the lower limit, respectively, in the expression (III). If the mean radiation temperature in half space II is assumed to be 20° C. one obtains at the lower limit $$t_{mrt_I} = 20 - 4.8 = 15.2° \text{ C. and}$$

$$\Delta\phi_n = 0.97 \times 5.75 \times 10^{-8} (20 + 273)^4 - (15.2 + 273)^4 = 26.3 \text{ W/m}^2 \tag{V},$$

and at the upper limit $$t_{mrt_I} = 20 + 7.8 = 27.8° \text{ C. and}$$

$$\Delta\phi_\phi = 0.97 \times 5.75 \times 10^{-8} (27.8 + 273)^4 - (20 + 273)^4 = 45.5 \text{ W/m}^2 \tag{VI}$$

Corresponding calculations can be performed for other values of $I_{clo}$.

It is possible to dimension a scale for the measuring instrument 24. The dimensioning becomes particularly simple if the areas and heating bodies of the probe plates are chosen in such a way that the voltage $E_{S1}'$ becomes equal to 0.1 × $\phi_F$, where $\phi_F$ is the power in W/m supplied to the probe plate.

Such an instrument scale 27 is shown in FIG. 4. The oblique lines 28 and 29 indicate the limits in the expression (I). As will be seen, the lines 28 and 29 are not parallel to the direction of the pointer of the instrument. This is due to the fact that the area, within which a person senses no thermal discomfort due to thermal asymmetry, expands the warmer the person is clothed. The areas 30 and 31, located outside the lines 28 and 29, may be marked with colors, for example blue and red, respectively. As will be seen, the lower and the upper limits are not located symmetrically in relation to the zero point of the instrument, and consequently it is necessary to give the probe a certain orientation so that it is always side I that faces the radiation source, which produces the asymmetry, or the air circulation. The said side is preferably marked on the probe, e.g. by means of a color code.

Since a person, as mentioned above, cannot feel whether asymmetrical heat emission is due to radiation or convection or a combination of both, one is justified in substituting the difference between the mean radiation temperatures, cf. expression (III), by the difference between the total heat emission from the two sides I and II. Consequently, the difference between the voltages $E_{S1}$ and $E_{S1}'$, which represent the heat emission from the two sides of the probe with a fairly high accuracy, will represent the asymmetry in the thermal field which a person will feel at the point where the probe is located.

FIG. 5 shows another embodiment of the probe. In this case two diametrically opposed black and dull plates 32 and 33 and two likewise diametrically opposed polished plates 34 and 35 have been placed on either side of the heat-insulating plate 1. With such a probe and a control and measuring equipment adapted thereto it is possible in addition to the measurement described above of the asymmetry of the thermal field also to perform a measurement of the air velocity and of the mean radiation temperature.

It will be possible to introduce the various clo-values electrically into the control and measuring equipment, whereby the scale of the instrument can be simplified, it being now possible to omit the curves shown in FIG. 4 which represent the different clo-values.

In the embodiment shown in FIG. 6 the probe comprises a plate 1 having a heat conduction figure and a heat capacity corresponding to those of the part of the skin situated outside the thermoreceptors, and a temperature dependent resistance 2, which by means of a known electronic control unit 3 maintains the plate at a constant temperature higher than the temperature of the surrounding air. The circuit illustrated in FIG. 3 but utilizing only one bridge circuit may be utilized. Thus, the signal $E_{S1}$ would be taken for example, across heating wire 4 corresponding to resistance wire 2 of FIG. 6. The resistance wire 2 may, as illustrated, alternately serve as a heating and temperature sensing element in a known manner. On the back side of the plate 1 a further plate 4 is glued having thermo dynamic properties corresponding to those of the part of the skin lying behind the thermoreceptors.

The power required to maintain the constant higher temperature is supplied to the resistance 2 in the form of square wave pulses, which means that the voltage across the resistor 2 is proprotional to the power supplied to the probe. When the probe is subjected to variations of the external influence, which are so slow that they can reach the resistor 2, they will bring about a variation in the voltage $E_{s1}$ across the resistor 2. This variation has the effect that the capacitors 5 and 6 will be charged to different voltages through the diodes 7 and 8 and the maximum amplitude can be read on the pointer instrument 8. Very slow variations of the external influences (<0.1 Hz) are not registered by thermoreceptors and they should therefore also not be read on the instrument 9. This is avoided by discharging the capacitors 5 and 6 through a variable resistor 10, which can be set to the desired resistance when the apparatus is calibrated.

In FIG. 7 a further refinement is shown for dealing with probes having a first thermal response time. It is well known that the partial differential equations describing the temperature destribution in a solid material through which heat flows and the voltage distribution along an arbitrary electric cable through which an electric current flows, are identical. Thus, an analogy exists between the electric and thermal systems. This is utilized in electric analog computers for the solution of non-stationary thermal problems. The embodiment shown in FIG. 7 is adapted for use in connection with very fast probes e.g. heating wire anemometers which have time constants as low as 0.001 second. The signal $E_{S2}$ from the probe passes through an attenuating circuit 11 consisting of resistors and capacitors which are so designed that they give the same attenuation and phase displacement of the electric signal as the plate 1 gives in the embodiment according to FIG. 6. This means that the signal when having passed the line A—A is identical to the signal $E_{S1}$ in FIG. 6. Thus, attenuating circuit 11 is designed such that variations in $E_{S2}$ of a frequency in the vicinity of 0.5 Hz are passed substantially unattenuated to instrument 9 whereas fast variations, e.g. of a frequency above 1 Hz, and slow variations, e.g. of a frequency below 0.1 Hz, are substantially damped.

The embodiment according to FIG. 7 can be connected to an existing anemometer for the direct measurement of the degree of thermal discomfort due to variations in air movement.

The invention is not, however, limited to the embodiments described above and shown in the drawings, but may be modified in various ways within the scope of the following patent claims.

What is claimed is:

1. Apparatus for measuring thermal discomfort originating from a draft, comprising
   an electrically heatable element exposed to the cooling effect of said draft,
   means for sensing the temperature of said heatable element,
   means for supplying electric energy to said heatable element in response to the sensed temperature so as to maintain said heatable element at a substantially constant, elevated temperature in relation to the ambient air in spite of the varying cooling effect of said draft,
   means for deriving from said electric energy delivered to said heatable element a first electrical signal which varies with the variations of the cooling effect of the draft on said heatable element,
   means for damping amplitude variations in the frequency ranges of said first electrical signal below approximately 0.1 Hz and above approximately 1 Hz in relation to the amplitude variations of said first electrical signal within this frequency range to produce a second electrical signal simulating the response of human thermoreceptors to draft conditions, and
   means for displaying said second electrical signal.

2. An apparatus as in claim 1 wherein said means for displaying is a meter.

3. An apparatus as in claim 2, wherein said heatable element is in the form of a plate having a thickness, a specific heat, and a heat conductivity corresponding to the depth of the thermoreceptors in, the specific heat of, and the heat conductivity of the human skin, respectively, said plate damping amplitude variations in said first electric signal having frequencies above approximately 1 Hz and wherein said first electric signal is supplied to said meter via an electric damping network substantially damping frequencies below approximately 0.1 Hz, the output of said damping network being said second electrical signal.

4. Apparatus as claimed in claim 2, wherein said first electric signal is serially supplied to said meter through a first electric damping network substantially damping frequencies above approximately 1 Hz and a second electric damping network substantially damping frequencies below approximately 0.1 Hz, the output from said first and second damping networks being said second electrical signal.

* * * * *